(12) United States Patent
Chen et al.

(10) Patent No.: US 8,398,671 B2
(45) Date of Patent: Mar. 19, 2013

(54) ELECTRICAL CONTACT FOR OCCLUSIVE DEVICE DELIVERY SYSTEM

(75) Inventors: Hancun Chen, Fremont, CA (US); Lantao Guo, San Ramon, CA (US); Jimmy Dao, San Jose, CA (US); Justin Vo, San Jose, CA (US); Michael Williams, Dover, NH (US); Richard Murphy, Sunnyvale, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 240 days.

(21) Appl. No.: 12/758,528

(22) Filed: Apr. 12, 2010

(65) Prior Publication Data
US 2010/0268252 A1  Oct. 21, 2010

Related U.S. Application Data

(60) Provisional application No. 61/170,043, filed on Apr. 16, 2009, provisional application No. 61/184,254, filed on Jun. 4, 2009.

(51) Int. Cl.
*A61M 29/00* (2006.01)
(52) U.S. Cl. ........................................ 606/200; 606/198
(58) Field of Classification Search .................. 606/108, 606/200, 32, 40, 49, 50, 191, 139, 157; 604/107, 604/57, 34, 41, 215; 600/372, 373, 377, 600/469, 499, 381, 382
See application file for complete search history.

(56) References Cited

U.S. PATENT DOCUMENTS

| | | | |
|---|---|---|---|
| 4,994,069 A | 2/1991 | Ritchart et al. | |
| 5,122,136 A * | 6/1992 | Guglielmi et al. | 606/32 |
| 5,226,911 A | 7/1993 | Chee et al. | |
| 5,304,194 A | 4/1994 | Chee et al. | |
| 5,382,259 A | 1/1995 | Phelps et al. | |
| 5,423,829 A * | 6/1995 | Pham et al. | 606/108 |
| 5,522,836 A * | 6/1996 | Palermo | 606/200 |
| 5,549,624 A | 8/1996 | Mirigian et al. | |
| 5,578,074 A * | 11/1996 | Mirigian | 606/108 |
| 5,582,619 A | 12/1996 | Ken | |
| 5,685,322 A * | 11/1997 | Sung et al. | 128/897 |

(Continued)

FOREIGN PATENT DOCUMENTS

| | | |
|---|---|---|
| DE | 10325130 | 9/2004 |
| EP | 0826342 A1 | 3/1998 |

(Continued)

OTHER PUBLICATIONS

PCT International Search Report and Written Opinion for PCT/US2010/030753 Applicant Boston Scientific Scimed, Inc., Forms PCT/ISA/210, 220, and 237 dated Sep. 20, 2010 (19 pages).

(Continued)

*Primary Examiner* — Ryan Severson
*Assistant Examiner* — David Eastwood
(74) *Attorney, Agent, or Firm* — Vista IP Law Group LLP

(57) ABSTRACT

A delivery wire assembly for delivery of an occlusive device to a location in a patient's vasculature includes a delivery wire conduit having a proximal tubular portion coupled to a distal coil portion, the respective tubular and coil portions defining a conduit lumen. A core wire is disposed in the conduit lumen and having a distal end coupled to an occlusive device, wherein an elongate electrical contact body at least partially seated in the conduit lumen and coupled to a proximal end of the core wire, the electrical contact body and the proximal tubular portion forming a junction. A coil collar is disposed around the electrical contact body near the junction.

12 Claims, 7 Drawing Sheets

U.S. PATENT DOCUMENTS

| | | | |
|---|---|---|---|
| 5,690,666 | A | 11/1997 | Berenstein et al. |
| 5,743,905 | A | 4/1998 | Eder et al. |
| 5,853,418 | A | 12/1998 | Ken et al. |
| 5,919,187 | A | 7/1999 | Guglielmi et al. |
| 5,984,929 | A | 11/1999 | Bashiri et al. |
| 6,059,779 | A | 5/2000 | Mills |
| 6,077,260 | A | 6/2000 | Wheelock et al. |
| 6,102,933 | A | 8/2000 | Lee et al. |
| 6,277,125 | B1 | 8/2001 | Barry et al. |
| 6,280,457 | B1 | 8/2001 | Wallace et al. |
| 6,409,721 | B1 | 6/2002 | Wheelock et al. |
| 6,468,266 | B1 | 10/2002 | Bashiri et al. |
| 6,537,293 | B1 | 3/2003 | Berryman et al. |
| 6,575,965 | B1 | 6/2003 | Fitch et al. |
| 6,589,230 | B2 | 7/2003 | Gia et al. |
| 6,953,473 | B2 | 10/2005 | Porter |
| 7,198,613 | B2 | 4/2007 | Gandhi et al. |
| 7,862,602 | B2 | 1/2011 | Licata et al. |
| 7,921,848 | B2 | 4/2011 | Nikolchev et al. |
| 2002/0091380 | A1 | 7/2002 | Wheelock et al. |
| 2002/0151883 | A1* | 10/2002 | Guglielmi ............... 606/32 |
| 2003/0120300 | A1 | 6/2003 | Porter |
| 2003/0130689 | A1 | 7/2003 | Wallace et al. |
| 2004/0002732 | A1 | 1/2004 | Teoh et al. |
| 2004/0002733 | A1 | 1/2004 | Teoh |
| 2004/0010243 | A1 | 1/2004 | Klint |
| 2006/0135986 | A1 | 6/2006 | Wallace et al. |
| 2006/0271097 | A1 | 11/2006 | Ramzipoor et al. |
| 2006/0282112 | A1 | 12/2006 | Griffin |
| 2007/0055302 | A1 | 3/2007 | Henry et al. |
| 2007/0073334 | A1* | 3/2007 | Ramzipoor ............... 606/200 |
| 2007/0123927 | A1 | 5/2007 | Faman |
| 2009/0018653 | A1 | 1/2009 | Bashiri et al. |
| 2009/0024154 | A1 | 1/2009 | Williams et al. |
| 2009/0062726 | A1* | 3/2009 | Ford et al. ............... 604/57 |
| 2009/0062812 | A1* | 3/2009 | Fitz et al. ............... 606/108 |
| 2009/0143786 | A1 | 6/2009 | Bashiri et al. |
| 2009/0177261 | A1 | 7/2009 | Teoh et al. |
| 2009/0299275 | A1 | 12/2009 | Gandhi et al. |
| 2010/0076479 | A1 | 3/2010 | Monstadt |
| 2010/0094395 | A1 | 4/2010 | Kellett |
| 2011/0160835 | A1 | 6/2011 | Licata et al. |

FOREIGN PATENT DOCUMENTS

| | | |
|---|---|---|
| WO | 9942038 | 8/1999 |
| WO | 03053281 | 7/2003 |
| WO | 2008085606 | 7/2003 |
| WO | WO2005070308 | 8/2005 |
| WO | 2008064206 | 5/2008 |
| WO | 2008144587 | 11/2008 |

OTHER PUBLICATIONS

PCT Invitation to Pay Additional Fees for International Application No. PCT/US2010/030753 Applicant Boston Scientific Scimed, Inc., Form PCT/ISA/206 and Annex to Form PCT/ISA/206, Communication Relating to the Results of the Partial International Search (4 pages).

Prosecution papers from related U.S. Appl. No. 12/122,636, filed May 16, 2008: Office Action mailed Nov. 12, 2010; Response filed Mar. 14, 2011; Office action mailed Jun. 7, 2011; Response filed Aug. 4, 2011; final Office Action mailed Jan. 20, 2012; Response filed Feb. 28, 2012.

Office Action mailed Jul. 15, 2011, in related European Application 08755795.5.

Documents from related International Application No. PCT/US2008/064013, filed May 16, 2008: International Search Report mailed May 18, 2009; Written Opinion mailed May 18, 2009; Invitation to Pay Additional Fees mailed Jan. 29, 2009; International Preliminary Report on Patentability mailed Dec. 3, 2009.

Documents from related International Application No. PCT/US2009/059797, filed Oct. 7, 2009: International Search Report mailed Nov. 30, 2009; Written Opinion mailed Nov. 30, 2009.

Documents from related International Application No. PCT/US2010/026831, filed Mar. 10, 2010: International Search Report mailed Dec. 13, 2010; Written Opinion mailed Dec. 13, 2010.

Documents from related International Application No. PCT/US2010/029700, filed Apr. 1, 2010: International Search Report mailed May 21, 2010; Written Opinion mailed May 21, 2010.

Non-final office action mailed Jun. 12, 2012 for related U.S. Appl. No. 12/720,965, filed Mar. 10, 2010, 10 pages.

* cited by examiner

ELECTRICAL CONTACT FOR OCCLUSIVE DEVICE DELIVERY SYSTEM

RELATED APPLICATION DATA

The present application claims the benefit under 35 U.S.C. §119 to U.S. provisional patent application Ser. Nos. 61/170,043, filed Apr. 16, 2009 and 61/184,254, filed Jun. 4, 2009. The foregoing applications are hereby incorporated by reference into the present application in their entirety.

FIELD OF THE INVENTION

The field of the invention generally relates to systems and delivery devices for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The relative stiffness of the coil will depend, among other things, on its composition, the diameter of the wire strand, the diameter of the primary mandrel, and the pitch of the resulting primary windings. The coil is then wrapped around a larger, "secondary" mandrel, and heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site in the vasculature, e.g., within an aneurismal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the delivery wire is extended out of the distal end opening of the micro-catheter and into the aneurysm. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher wire completes a circuit with a return electrode, and the detachment zone disintegrates due to electrolysis.

In "monopolar" systems, return electrodes include electrodes attached to the patient's skin and conductive needles inserted through the skin at a remote site. In "bipolar" systems, return electrodes are located on the pusher wire but electrically insulated from the conductive path ending in the detachment zone.

The anode is made up of an insulated core wire, which runs through the pusher wire, is attached to the electrical contact at the proximal end, and forms the detachment zone at the distal end. The anode electrical contact is a metallic tube secured to the proximal end of the pusher wire.

Perceived problems with current vaso-occlusive coil delivery systems include lack of stability at the junction where the metallic tube is secured to the proximal end of the pusher wire. Both orthogonal and axial forces may be exerted on the junction when the pusher wire is positioned in the micro-catheter and when the anode electrical contract is connected to and disconnected from the power supply. These forces may lead to kinking and buckling of the pusher wire. These forces may also damage the junction and may adversely impact detachment of the embolic coil by electrolysis.

SUMMARY

In one embodiment, a delivery wire assembly for delivery of an occlusive device to a location in a patient's vasculature includes a delivery wire conduit having a proximal tubular portion coupled to a distal coil portion, the respective tubular and coil portions defining a conduit lumen, wherein the proximal tubular portion tapers down in cross section at a proximal end thereof, and a core wire disposed in the conduit lumen and having a distal end coupled to an occlusive device. The delivery wire assembly also includes an electrical contact coupled to a proximal end of the core wire, wherein the electrical contact includes a connection collar. The connection may be a metal tube or a metal coil. The electrical contact and the core wire form an anode of an electrolytic detachment circuit for detaching the occlusive device from the core wire. Further, the delivery wire assembly includes a ground contact, where the electrical contact and the core wire form a first conductive path, and the ground contact and the delivery wire conduit form a second conductive path. The delivery wire assembly also includes a sleeve disposed around at least a portion of the delivery wire conduit. The sleeve is secured to the delivery wire conduit by heat lamination.

In another embodiment, an occlusive coil delivery system includes a delivery catheter, a delivery wire assembly, and a power supply. The delivery catheter includes a proximal end, a distal end, and a catheter lumen extending between the proximal and distal ends. The delivery wire assembly includes a delivery wire conduit having a proximal tubular portion coupled to a distal coil portion, the respective tubular and coil portions defining a conduit lumen, where the proximal tubular portion tapers down in cross section at a proximal end thereof, and a core wire disposed in the conduit lumen and having a distal end coupled to an occlusive coil. The delivery wire assembly also includes an electrical contact coupled to a proximal end of the core wire, the electrical contact and core wire forming an anode of an electrolytic detachment circuit for detaching the occlusive coil from the core wire. The electrical contact includes a connection collar. The power supply is electrically connected to the core wire. Further, the delivery wire assembly includes a ground contact, where the electrical contact and the core wire form a first conductive path, the ground contact and the delivery wire conduit form a second conductive path, and the power supply is electrically connected to the respective first and second conductive paths.

In yet another embodiment, a delivery wire assembly for delivery of an occlusive device to a location in a patient's vasculature includes a delivery wire conduit having a proximal tubular portion coupled to a distal coil portion, the respective tubular and coil portions defining a conduit lumen and a core wire disposed in the conduit lumen and having a distal end coupled to an occlusive device. The delivery wire assembly also includes an elongate electrical contact body at least partially seated in the conduit lumen and coupled to a proximal end of the core wire, the electrical contact body and the proximal tubular portion forming a junction and a coil collar disposed around the electrical contact body near the junction. The electrical contact body may be a tube, a tubular body mode of coils, or a mandrel. The electrical contact body is coupled to the proximal tubular portion with a soldering bond. The coil collar is coupled to the electrical contact body and the proximal tubular portion with an adhesive or a soldering bond. The electrical contact body is coupled to the core wire with a soldering bond or a welding bond. The coil collar has an open pitch in the range of 10% to 15%. Further, the delivery wire assembly includes a ground contact, where the electrical contact body and the core wire form a conductive path, and the ground contact and the delivery wire conduit form a second conductive path.

In still another embodiment, a delivery wire assembly includes a delivery wire conduit having a proximal tubular portion coupled to a distal coil portion, the respective tubular and coil portions defining a conduit lumen, a core wire disposed in the conduit lumen and having a distal end coupled to an occlusive coil, an elongate electrical contact body at least partially seated in the conduit lumen and coupled to a proximal end of the core wire, and the electrical contact body and the proximal tubular portion forming a junction. The delivery wire conduit also includes a proximal end, where the inner surface of the proximal end flares out in a proximal direction.

BRIEF DESCRIPTION OF THE DRAWINGS

Referring now to the drawings in which like reference numbers represent corresponding parts throughout, and in which.

DETAILED DESCRIPTION OF THE
ILLUSTRATED EMBODIMENTS

Figure 1:
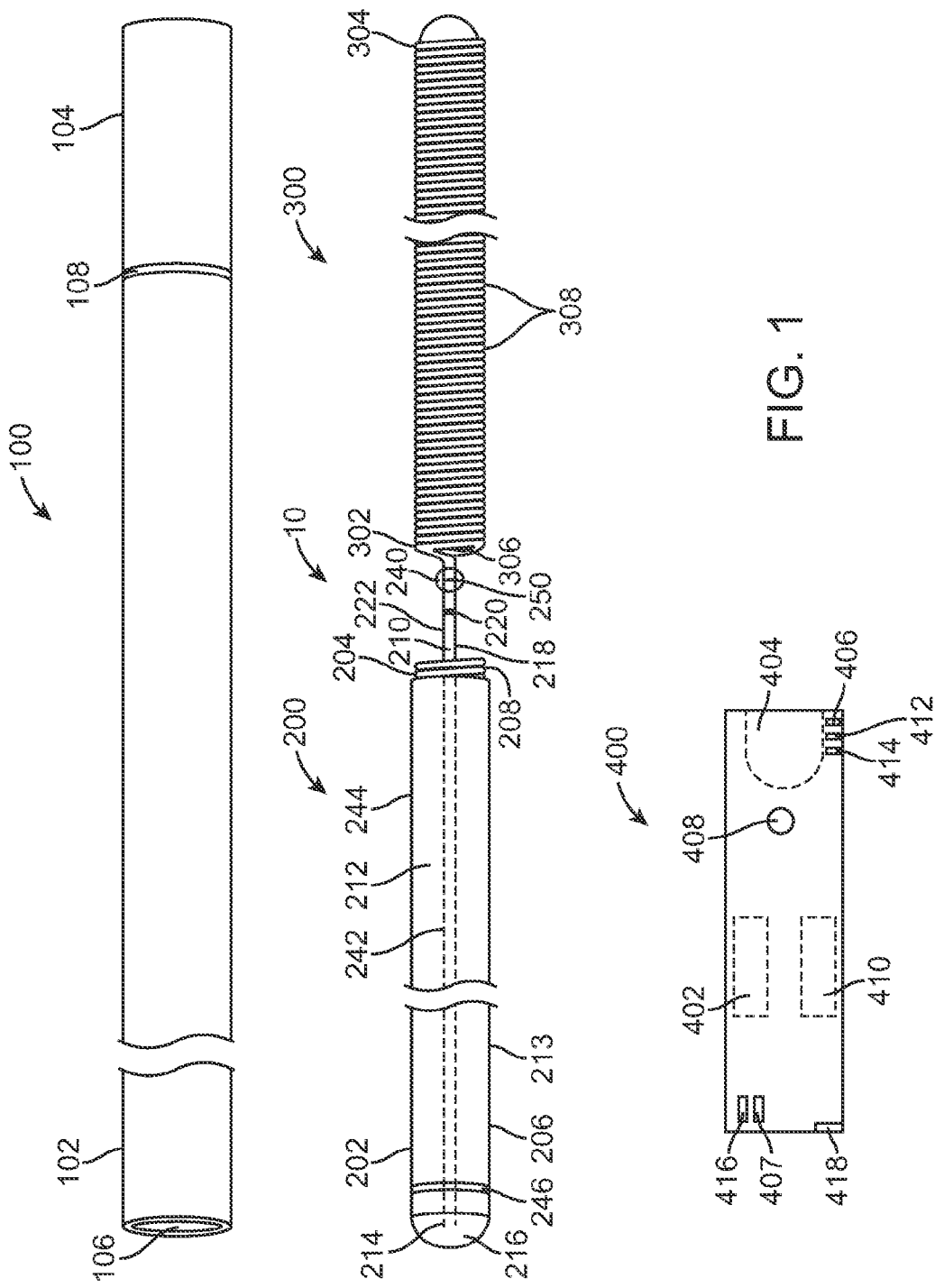
FIG. 1 illustrates an occlusive coil delivery system, according to one embodiment.

FIG. 1 illustrates an occlusive coil delivery system 10 according to one embodiment of the invention. The system 10 includes a number of subcomponents or sub-systems, including a delivery catheter 100, a delivery wire assembly 200, an occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the delivery wire assembly 200. Further, the lumen 106 is sized for the passage of a guidewire (not shown), which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100.

The inner lumen 106 is advantageously coated with a lubricious coating such as PTFE to reduce frictional forces between the delivery catheter 100 and the respective delivery wire assembly 200 and occlusive coil 300 being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective delivery wire assembly 200 and occlusive coil 300, but generally the diameter lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Still referring to FIG. 1, the system 10 includes a delivery wire assembly 200 configured for axial movement within the lumen 106 of the delivery catheter 100. The delivery wire assembly 200 generally includes a proximal end 202 and a distal end 204. The delivery wire assembly 200 includes a delivery wire conduit 213, which has a proximal tubular portion 206 and a distal coil portion 208. The proximal tubular portion 206 may be formed from, for example, a flexible stainless steel hypotube. The distal coil portion 208 may be formed from, for example, stainless steel wire. The distal coil portion 208 may be bonded to the proximal tubular portion 206 in an end-to-end arrangement.

The delivery wire assembly 200 further includes a core wire 210 that extends from the proximal end 202 of the delivery wire assembly 200 to a location that is distal with respect to the distal end 204 of the delivery wire assembly 200. The core wire 210 is disposed within a conduit lumen 212 that extends within an interior portion of the delivery wire conduit 213. The core wire 210 is formed from an electrically conductive material such as stainless steel wire. The proximal end 214 of the core wire 210 (shown in phantom) is electrically coupled to an electrical contact 216 located at the proximal end 202 of the delivery wire assembly 200. The electrical contact 216 is configured to interface with a corresponding electrical contact (not shown) in the power supply 400.

A portion of the core wire 210 is advantageously coated with an insulative coating 218. The insulative coating 218 may include polyimide. The entire length of the core wire 210 is coated with an insulative coating 218, except for the proximal end 214 of the core wire 210 that contacts the electrical contact 216, and a small region 220 located in a portion of the core wire 210 that extends distally with respect to the distal end 204 of the delivery wire assembly 200. This latter, "bare" portion of the core wire 210 forms the electrolytic detachment zone 220, which dissolves upon application of electrical current from the power supply 400.

Still referring to FIG. 1, the occlusive coil 300 includes a proximal end 302, a distal end 304, and a lumen 306 extending there between. The occlusive coil 300 is generally made from a biocompatible metal such as platinum or a platinum alloy (e.g., platinum-tungsten alloy). The occlusive coil 300 generally includes a straight configuration (as illustrated in FIG. 1) when the occlusive coil 300 is loaded within the delivery catheter 100. Upon release, the occlusive coil 300 generally takes a secondary shape which may include two-dimensional or three-dimensional configurations such as that illustrated in FIG. 3. The occlusive coil 300 includes a plurality of coil windings 308. The coil windings 308 are generally helical about a central axis disposed along the lumen 306 of the occlusive coil 300. The occlusive coil 300 may have a closed pitch configuration as illustrated in FIG. 1. Of course, the system 10 described herein may be used with occlusive coils 300 or other occlusive structures having a variety of configurations, and is not limited to occlusive coils 300 having a certain size or configuration.

The distal end 222 of the core wire 210 is connected to the proximal end 302 of the occlusive coil 300 at a junction 250. Various techniques and devices can be used to connect the core wire 210 to the occlusive coil 300, including laser melting, and laser tack, spot, and continuous welding. It is preferable to apply an adhesive 240 to cover the junction 250 formed between the distal end 222 of the core wire 210 and the proximal end 302 of the occlusion coil 300. The adhesive 240 may include an epoxy material which is cured or hardened through the application of heat or UV radiation. For example, the adhesive 240 may include a thermally cured, two-part epoxy such as EPO-TEK® 353ND-4 available from Epoxy Technology, Inc., 14 Fortune Drive, Billerica, Mass. The adhesive 240 encapsulates the junction 250 and increases its mechanical stability.

Still referring to FIG. 1, the system 10 further includes a power supply 400 for supplying direct current to the core wire 210, which contains the electrolytic detachment zone 220. In the presence of an electrically conductive fluid (including a physiological fluid such as blood, or an electrically conductive flushing solution such as saline), activation of the power supply 400 causes electrical current to flow in a circuit including the electrical contact 216, the core wire 210, the electrolytic detachment zone 220, and a return electrode (not shown—typically a needle attached to the patient's skin). After several seconds (generally less than about 10 seconds), the sacrificial electrolytic detachment zone 220 dissolves, and the occlusive coil 300 separates form the core wire 210.

The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the electrical contact 216 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 407 is activated if the onboard energy source needs to be recharged or replaced. The power supply 400 includes an activation trigger or button 408 that is depressed by the user to apply the electrical current to the sacrificial electrolytic detachment zone 220. Once the activation trigger 408 has been activated, the driver circuitry 402 automatically supplies current until detachment occurs. The drive circuitry 402 typically operates by applying a substantially constant current, e.g., around 1.5 mA.

The power supply 400 may include optional detection circuitry 410 that is configured to detect when the occlusive coil 300 has detached from the core wire 210. The detection circuitry 410 may identify detachment based upon a measured impedance value. A visual indicator 412 may indicate when the power supply 400 is being supplied to the current to the sacrificial electrolytic detachment zone 220. Another visual indicator 414 may indicate when the occlusive coil 300 has detached from the core wire 210. As an alternative to the visual indicator 414, an audible signal (e.g., beep) or even tactile signal (e.g., vibration or buzzer) may be triggered upon detachment. The detection circuitry 410 may be configured to disable the drive circuitry 402 upon sensing detachment of the occlusive coil 300.

The power supply 400 may also contain another visual indicator 416 that indicates to the operator when non-bipolar delivery wire assembly is inserted into the power supply 400. As explained in the background above, non-bipolar delivery wire assemblies use a separate return electrode that typically is in the form of a needle that was inserted into the groin area of the patient. The power supply 400 is configured to detect when a non-bipolar delivery wire assembly has been inserted. Under such situations, the visual indicator 416 (e.g., LED) is turned on and the user is advised to insert the separate return electrode (not shown in FIG. 1) into a port 418 located on the power supply 400.

Still referring to FIG. 1, the core wire 210 forms a first conductive path 242 between the electrical contact 216 and the electrolytic detachment zone 220. This first conductive path 242 may comprise the anode (+) of the electrolytic circuit when the delivery wire assembly 200 is operatively coupled to the power supply 400. A second conductive path 244, the return path, is formed by the proximal tubular portion 206 and a distal coil portion 208 of the delivery wire conduit 213. The second conductive path 244 is electrically isolated from the first conductive path 242. The second conductive path 244 may comprise the cathode (−) or ground electrode for the electrical circuit.

Figure 2:
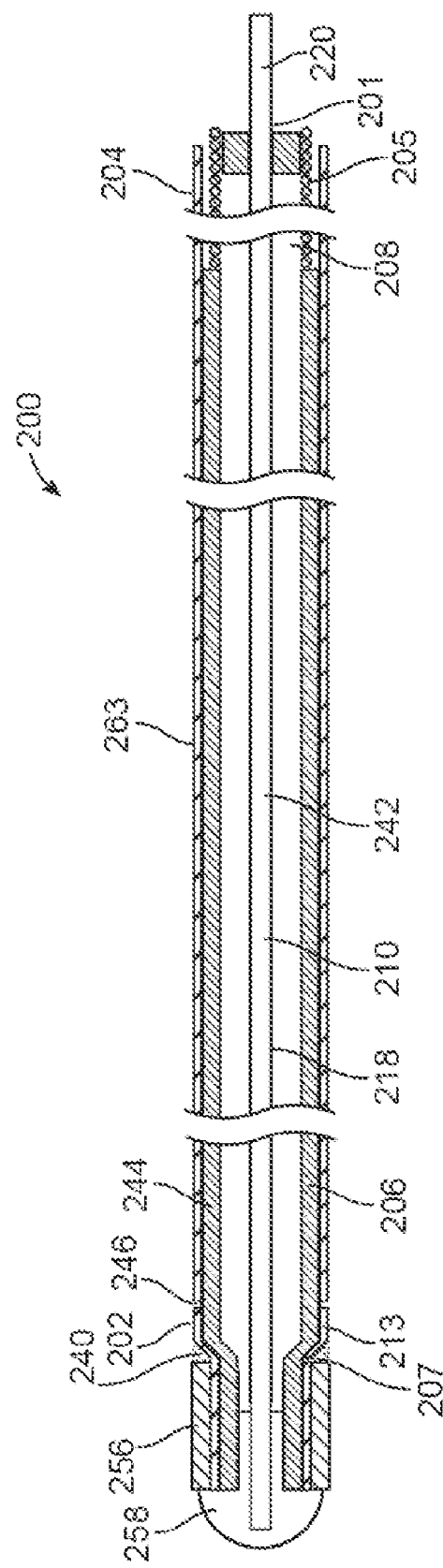
FIG. 2 is a longitudinal cross-sectional view of a delivery wire assembly, according to one embodiment.

A ground contact 246 for the second conductive path 244 may be disposed on a proximal end of the tubular portion 206 of the delivery wire conduit 213. In one embodiment, the ground contact 246 is simply an exposed portion of the tubular portion 206 since the tubular portion 206 is part of the second conductive path 244. For instance, a proximal portion of the tubular portion 206 that is adjacent to the electrical contact 216 may be covered with an insulative coating 207 such as polyimide as illustrated in FIG. 2. An exposed region of the tubular portion 206 that does not have the insulative coating may form the ground contact 246. Alternatively, the ground contact 246 may be a ring type electrode or other contact that is formed on the exterior of the tubular portion 206.

The ground contact 246 is configured to interface with a corresponding electrical contact (not shown) in the power supply 400 when the proximal end 202 of the delivery wire assembly 200 is inserted into the power supply 400. The ground contact 246 of the second conductive path 244 is, of course, electrically isolated with respect to the electrical contact 216 of the first conductive path 242.

FIG. 2 illustrates a cross-sectional view of the delivery wire assembly 200 according to one embodiment. Similar elements of this embodiment are identified with the same reference numbers as discussed above with respect to FIG. 1. The delivery wire assembly 200 includes a proximal end 202 and a distal end 204 and measures between around 184 cm to around 186 cm in length. The delivery wire assembly 200 includes a delivery wire conduit 213 with a proximal tubular portion 206 and a distal coil portion 208. The proximal tubular portion 206 may be formed from stainless steel hypotube having an outer diameter (OD) of 0.013 inches and inner diameter (ID) of 0.005 inches. The length of the hypotube section may be between around 140 cm to around 150 cm, although other lengths may also be used.

Figure 4:
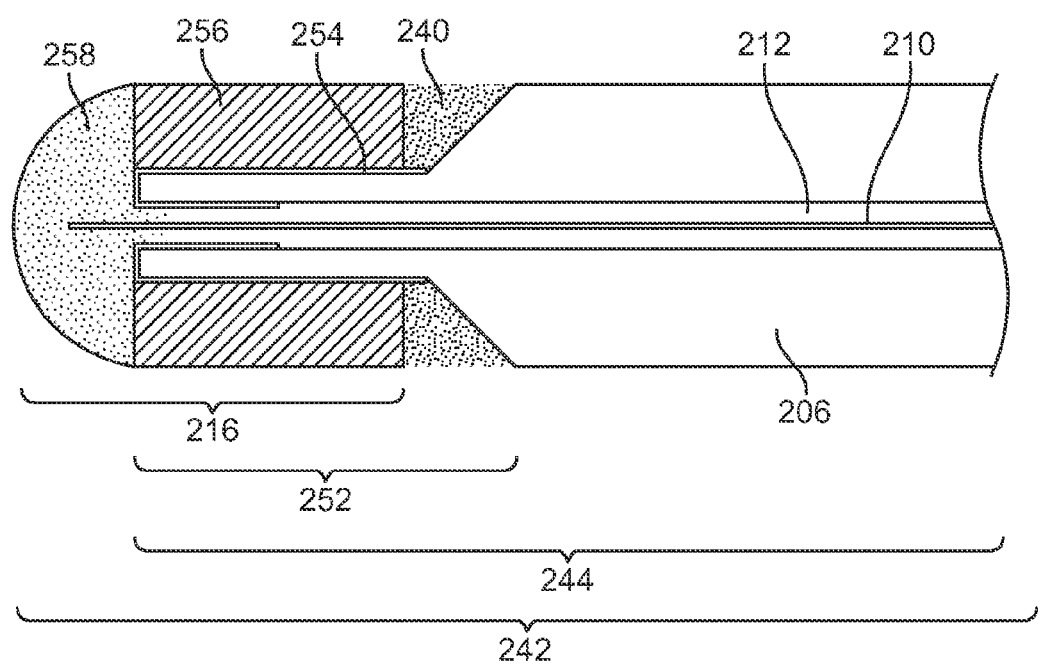
FIGS. 4 to 9 are detailed longitudinal cross-sectional views of delivery wire assemblies, according to various embodiments, wherein the outside sleeve has been omitted for clarity.
Figure 5:
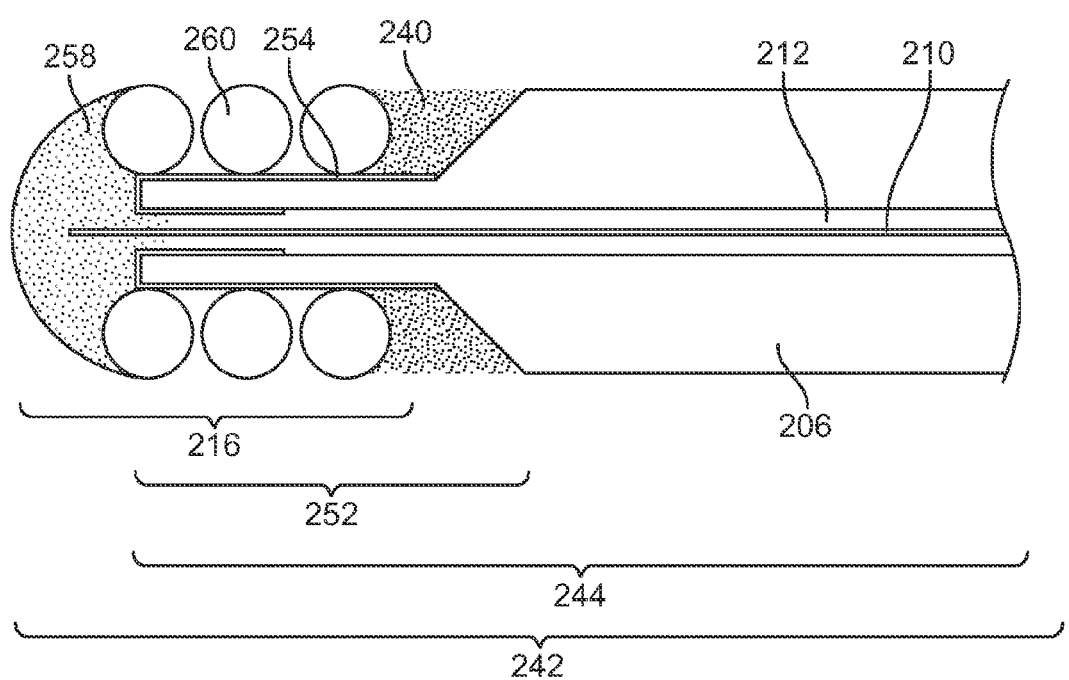

As seen in FIGS. 2, 4, and 5, the proximal end 252 of the proximal tubular portion 206 tapers down to relatively small cross section. In particular, in the embodiment depicted in FIGS. 2 and 4, the OD of the proximal end 252 of the proximal tubular portion 206 is approximately 0.009 inches, whereas the OD of the rest of the proximal tubular portion 206 is approximately 0.013 inches. The ID remains constant at 0.005 inches throughout the length of the proximal tubular portion 206. The proximal end 252 of the proximal tubular portion 206 is covered, both externally and at least partially in the conduit lumen 212, with an insulation layer 254.

In FIGS. 2 and 4, a connection tube 256 is disposed like a connection collar around the insulation layer 254, which separates it electrically from the proximal tubular portion 206. The connection tube 256 has an OD of approximately 0.013 inches to match the main body of the proximal tubular portion 206, and an ID of 0.0100, slightly larger than the OD of the proximal end 252 of the proximal tubular portion 206. The connection tube 256 is electrically and physically connected to the core wire 210 with a silver epoxy 258, which is applied to the connection tube 256, the insulation 254 covered proximal end 252 of the proximal tubular portion 206, and that end of the core wire 210. After the silver epoxy 258 is allowed to cure, clippers or the like may be used to trim the excess material. The connection tube 256 is also physically connected to the proximal end 252 of the proximal tubular portion 206 with the silver epoxy 258 and a non-conductive adhesive 240. The connection tube 256 and the cured silver epoxy 258 form the electrical contact 216, which along with the core wire 210 form the first conductive path 242 and the anode. The insulation layer 254 electrically separates the first conductive path 242 from the proximal tubular portion 206, which is part of the second (return) conductive path 244.

The embodiment depicted in FIG. 5 is similar to that depicted in FIGS. 2 and 4, except that the connection tube 256 has been replaced with a connection coil 260, which forms the connection collar. The connection coil 260 has dimensions similar to the connection tube 256 and it has open pitch coils. The pitch of the coils is around 5-40%, preferably around 10-30%, and more preferably around 10-20%. The connection coil 260 increases the flexibility of the proximal end 252 of the proximal tubular portion 206, which in turn increases its structural integrity.

Figure 6:
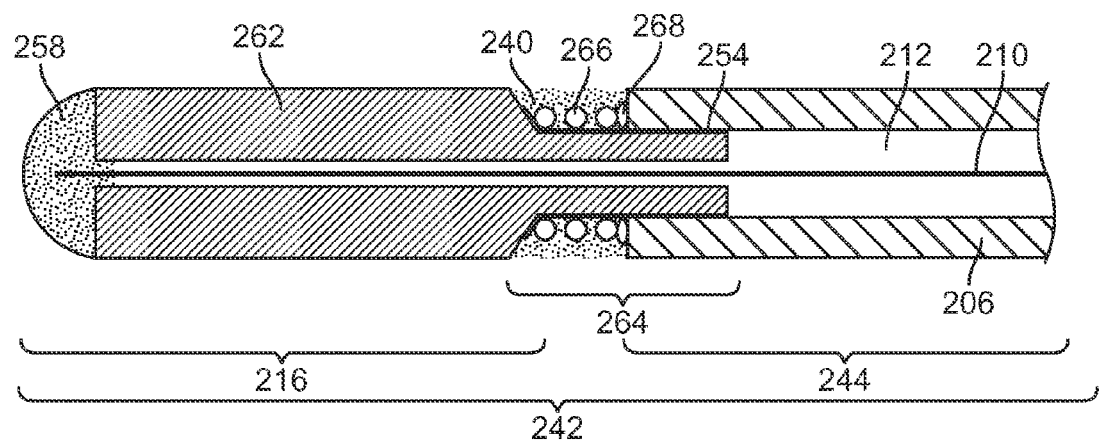
Figure 8:
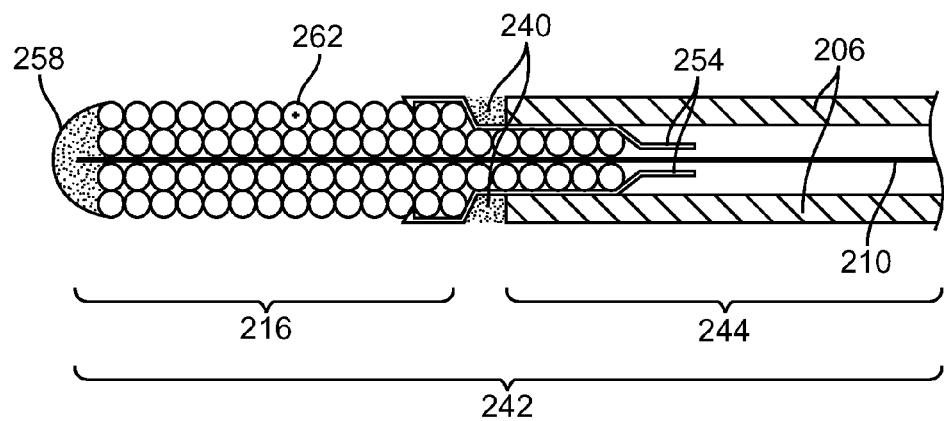

In another embodiment, shown in FIG. 6, the proximal tubular portion 206 does not taper down to a smaller cross section. A proximal contact tube 262 is seated in the conduit lumen 212, forming a junction 264, and the core wire 210 is threaded through the proximal contact tube 262. The proximal contact tube 262 is an elongate body that may be made of Nitinol or stainless steel. Alternatively, the proximal contact tube 262 may be a tubular body formed from stainless steel coils, as depicted in FIG. 8. The proximal contact tube 262 is connected to the proximal tubular portion 206 with non-conductive adhesive 240 near the junction 264. The proximal contact tube 262 is also connected to the core wire 210 with a silver epoxy 258 where the core wire 210 extends out of the proximal end of the proximal contact tube 262. The proximal contact tube 262 and the silver epoxy 258 form the electrical contact 216, which along with the core wire 210 form the first conductive path 242 and the anode. An insulation layer 254 electrically separates the proximal contact tube 262 from the proximal tubular portion 206. Embedded in the adhesive 240 around the junction 264 is a coil collar 266, which increases the flexibility of the junction 264, which in turn increases its structural integrity. The coil has an open pitch of around 10% to 15%. The coil collar 266 is connected to the proximal tubular portion 206 with a soldering bond 268, which also connects the proximal contact tube 262 with the proximal tubular portion 206.

Figure 7:
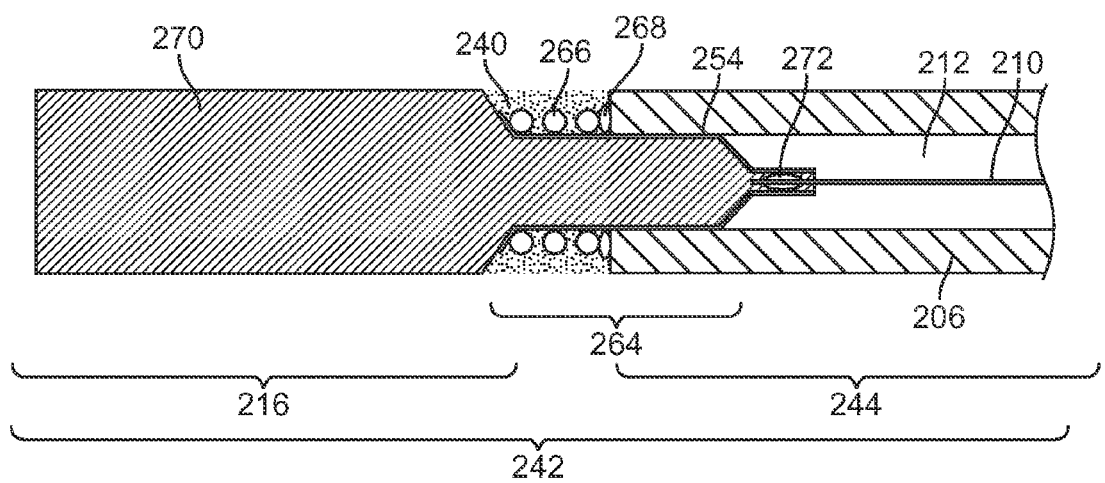

The embodiment depicted in FIG. 7 is similar to that depicted in FIG. 6, except that the proximal contact tube 262 has been replaced with a proximal contact mandrel 270. The core wire 210 is joined to the distal end of the proximal contact mandrel 270 with a conductive bond 272, such as that formed by welding or soldering. The function of the structure and function of the coil collar 266 remains unchanged in this embodiment.

Figure 9:
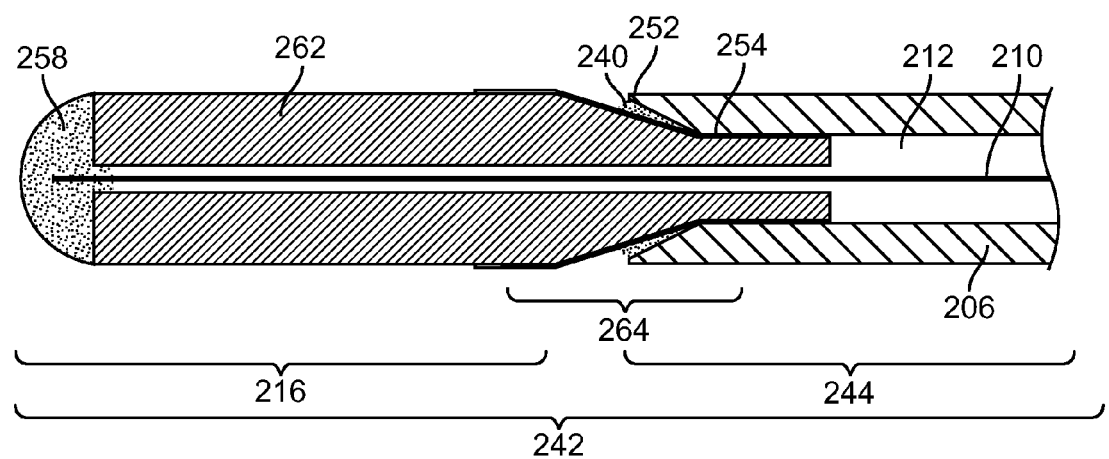

In the embodiment shown in FIG. 9, the inner surface of the proximal end 252 of the proximal tubular portion 206 of the delivery wire conduit 213 flares out in a proximal direction such that the ID of the proximal end 252 of the proximal tubular portion 206 is larger than the ID of the rest of the proximal tubular portion 206. The flaring of the inner surface at the proximal end 252 reduces stress concentration at the junction 264 where the proximal contact tube 262 is seated in the conduit lumen 212, thereby reducing the tendency of buckling when the junction 264 is compressed. An adhesive 240 seals and bonds the junction 264.

As seen in FIG. 2, a distal coil portion 208 is bonded in end-to-end fashion to the distal face of the proximal tubular portion 206. The bonding may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil.

One or more marker coils 205 of the distal coil portion 208 may be formed from a radiopaque material (illustrated as solid marker coils 205 in distal coil portion 208). For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 263 or jacket surrounds a portion of the proximal tubular portion 206 and a portion of the distal coil portion 208 of the delivery wire conduit 213. The outer sleeve 263 covers the interface or joint formed between the proximal tubular portion 206 and the distal coil portion 208. The outer sleeve 263 may have a length of around 50 cm to around 54 cm. The outer sleeve 263 may be formed from a polyether block amide plastic material (e.g., PEBAX 7233 lamination). The outer sleeve 263 may include a lamination of PEBAX and HYDROLENE® that may be heat laminated to the delivery wire assembly 200. The OD of the outer sleeve 263 may be less than 0.02 inches and advantageously less than 0.015 inches.

The core wire 210, which runs through the delivery wire conduit 213, terminates at electrical contact 216 at one end and extends distally with respect to the distal coil portion 208 of the delivery wire conduit 213. The core wire 210 is coated with an insulative coating 218 such as polyimide except at the electrolytic detachment zone 220 and the proximal segment coupled to the electrical contact 216. The electrolytic detachment zone 220 is located several centimeters (e.g., about 0.02 mm to about 0.2 mm) distally with respect to the distal end of the distal coil portion 208. The core wire 210 may have an OD of around 0.00175 inches.

Figure 3:
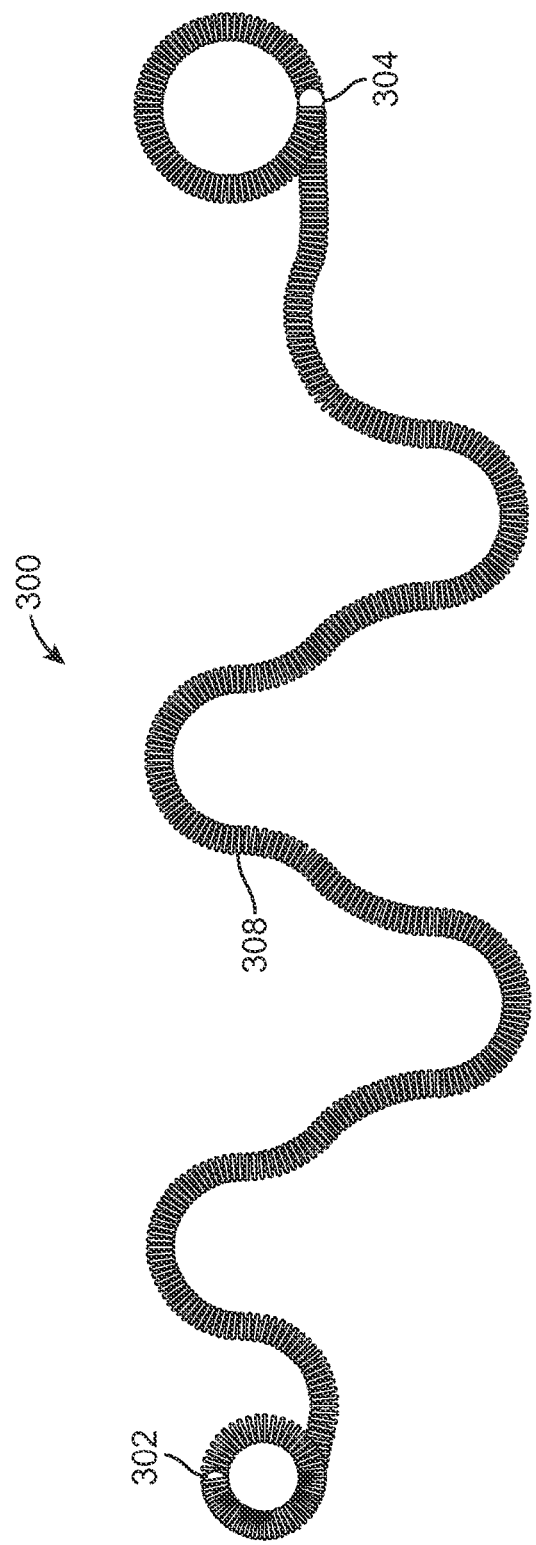
FIG. 3 illustrates an occlusive coil in a natural state mode, illustrating one exemplary secondary configuration.

FIG. 3 illustrates one exemplary configuration of an occlusive coil 300 in a natural state. In the natural state, the occlusive coil 300 transforms from the straight configuration illustrated in, for instance, FIG. 1 into a secondary shape. The secondary shaped may include both two and three dimensional shapes of a wide variety. FIG. 3 is just one example of a secondary shape of an occlusive coil 300 and other shapes and configurations are contemplated to fall within the scope of the invention. Also, the occlusive coil 300 may incorporate synthetic fibers over all or a portion of the occlusive coil 300 as is known in the art. These fibers may be attached directly to coil windings 308 or the fibers may be integrated into the occlusive coil 300 using a weave or braided configuration.

While various embodiments of the present invention have been shown and described, they are presented for purposes of illustration, and not limitation. Various modifications may be made to the illustrated and described embodiments without departing from the scope of the present invention, which is to be limited and defined only by the following claims and their equivalents.

What is claimed is:

1. A delivery wire assembly for delivery of an occlusive device to a location in a patient's vasculature, comprising:
   a delivery wire conduit having a proximal tubular portion coupled to a distal coil portion, the respective tubular and coil portions defining a conduit lumen, wherein a proximal end of the proximal tubular portion tapers down in cross section in a proximal direction from a distal larger diameter region to a proximal smaller diameter region;
   a core wire disposed in the conduit lumen, the core wire having a distal end detachably coupled to an occlusive device; and
   an electrical contact coupled to a proximal end of the core wire and disposed around the smaller diameter region of the proximal tubular portion of the delivery wire conduit, the electrical contact and Core wire forming a first conductive path, wherein the electrical contact has first and second longitudinal ends, and wherein the first longitudinal end is coupled to the proximal tubular portion of the delivery wire conduit and to the core wire with an electrically conductive adhesive.

2. The delivery wire assembly of claim 1, wherein the electrical contact comprises a connection collar in the form of a metal tube.

3. The delivery wire assembly of claim 1, further comprising a ground contact, wherein the delivery wire conduit and ground contact form a second conductive path.

4. The delivery wire assembly of claim 1, the electrical contact and core wire forming an anode of an electrolytic detachment circuit for detaching the occlusive device from the core wire.

5. The delivery wire assembly of claim 1, further comprising a sleeve disposed around and secured to at least a portion of the delivery wire conduit.

6. An occlusive coil delivery system, comprising:
   a delivery catheter comprising a proximal end, a distal end, and a catheter lumen extending between the proximal and distal ends;
   a delivery wire assembly comprising
   a delivery wire conduit having a proximal tubular portion coupled to a distal coil portion, the respective tubular and coil portions defining a conduit lumen, wherein a proximal end of the proximal tubular portion tapers down in cross section in a proximal direction from a distal larger diameter region to a proximal smaller diameter region,
   a core wire disposed in the conduit lumen and having a distal end detachably coupled to an occlusive coil, and
   an electrical contact coupled to a proximal end of the core wire and disposed around the smaller diameter region of the proximal tubular portion of the delivery wire conduit, the electrical contact and core wire forming an anode of an electrolytic detachment circuit for detaching the occlusive coil from the core wire, wherein the electrical contact has first and second longitudinal ends, wherein the first longitudinal end is coupled to the proximal tubular portion of the delivery wire conduit and to the core wire with an electrically conductive adhesive; and a power supply electrically connected to the core wire.

7. The delivery system of claim 6, wherein the electrical contact comprises a connection collar.

8. The delivery system of claim 6, further comprising a ground contact, wherein the electrical contact and the core wire form a first conductive path, the ground contact and the delivery wire conduit form a second conductive path, and the power supply is electrically connected to the respective first and second conductive paths.

9. The delivery wire assembly of claim 6, wherein the second longitudinal end is coupled to the proximal tubular portion of the delivery wire conduit with a non-electrically conductive adhesive.

10. The delivery wire assembly of claim 6, wherein the electrical contact is not disposed around the larger diameter region of the proximal tubular portion of the delivery wire conduit.

11. The delivery system of claim 1, wherein the electrical contact is not disposed around the larger diameter region of the proximal tubular portion of the delivery wire conduit.

12. The delivery wire assembly of claim 1, wherein the second longitudinal end is coupled to the proximal tubular portion of the delivery wire conduit with a non-electrically conductive adhesive.

* * * * *